United States Patent [19]

Sawhill et al.

[11] Patent Number: 5,384,092
[45] Date of Patent: Jan. 24, 1995

[54] TREATMENT OF INFECTIOUS WASTES

[76] Inventors: James W. Sawhill, 20803 Bryant St., Canoga Park, Calif. 01306; Leon D. Freeman, 49 Alta Way, Corte Madera, Calif. 94925; Carl McKinney, 1357 W. Meseto, Mesa, Ariz. 85202

[21] Appl. No.: 47,276

[22] Filed: Apr. 19, 1993

[51] Int. Cl.$^6$ .................... A61L 2/18; B02C 23/26
[52] U.S. Cl. .......................... 422/32; 241/17; 241/21; 241/606; 241/DIG. 38; 422/28; 435/262.5
[58] Field of Search ............ 422/32, 37, 202, 184, 422/28, 30; 241/606, DIG. 38, 16, 17, 21; 588/205; 435/219, 220, 262, 262.5; 252/174.12, DIG. 12

[56] References Cited

U.S. PATENT DOCUMENTS

| | | | |
|---|---|---|---|
| 4,036,993 | 7/1977 | Ikeda et al. | 435/267 |
| 4,038,184 | 7/1977 | Svanteson | 241/17 |
| 4,473,589 | 9/1984 | Freeman et al. | 435/69 |
| 5,089,228 | 2/1992 | Meijer | 422/37 |
| 5,139,204 | 8/1992 | Shawlet et al. | 241/21 |
| 5,190,725 | 3/1993 | Meijer et al. | 422/37 |

Primary Examiner—Robert J. Warden
Assistant Examiner—L. M. Crawford
Attorney, Agent, or Firm—Plante & Strauss

[57] ABSTRACT

There is disclosed the sterilization of infectious hospital waste to generating a residue which is suitable for disposal. The invention comprises a first step of digestion at elevated temperatures and under highly alkaline condition for one to three hours. This step is combined with the necessary comminution, e.g., grinding, pulverizing and the like, to ensure substantially complete liquefaction of the wastes. The liquid reaction products from the first step are neutralized to a slightly alkaline pH, e.g., 7.5–9.5, and the waste is then subjected to enzymatic digestion with a suitable proteolytic enzyme for a short period of time. Preferably this proteinase treatment is combined with further comminution to further reduce any oversized particles that may remain in the waste following the first treatment. The enzymatic treatment is continued for a period from 30 to 90 minutes at temperatures most suitable for the selected enzyme and results in substantially complete hydrolysis of the proteins in the waste. Finally, the treated waste from the second step of enzymatic digestion is inoculated with from 8 to 20 percent of a sterilant, preferably sodium hypochlorite and the pH is reduced to an acidic pH from about 3 to about 6, and the inoculated residue is held for an extended period of time, from about 30 to about 120 minutes at an elevated temperature to ensure essentially complete sterilization of the liquid which can be concentrated or dried for disposal.

13 Claims, 1 Drawing Sheet

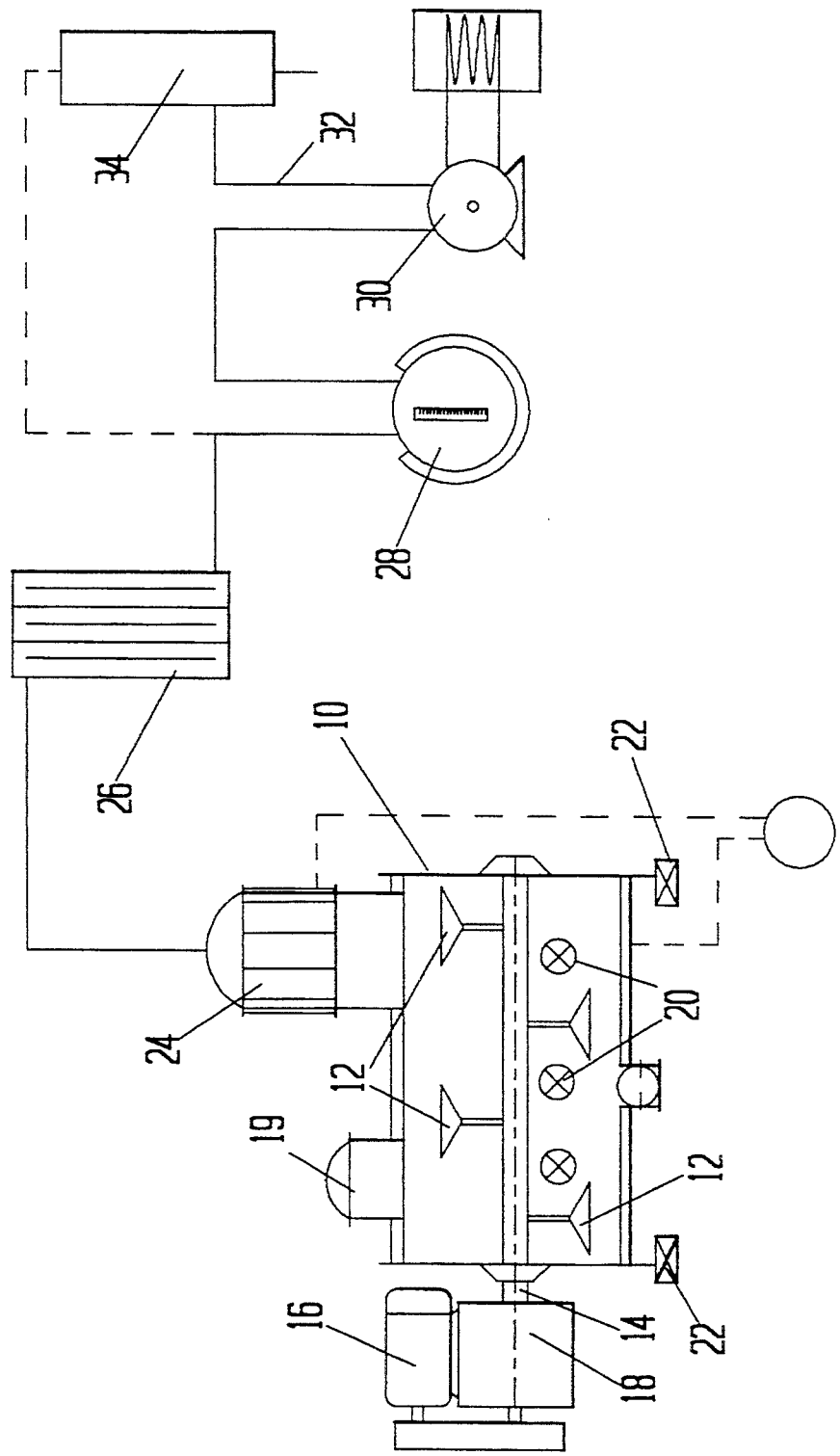

TREATMENT OF INFECTIOUS WASTES

BACKGROUND OF THE INVENTION

1. Field of Invention

This invention relates to a method for the treatment of infectious wastes and, in particular, for the treatment of "red bag" hospital wastes

2. Brief Statement of the Prior Art

The efficient and sanitary disposal of infectious wastes, particularly "red bag" hospital waste is a problem of increasing concern in most communities. The most common disposal method is in landfills, however, this method is clearly not the best suited with modern technology, particularly since pathogens in such waste are extremely resistant and can exist as spores and other infectious forms for many years in the soil.

Infectious hospital waste have also been burned in incinerators. While incineration would theoretically be an efficient method for disposal of such waste, there are problems presented by the variation in composition of the wastes and the inclusion in the waste of halogenated plastics such as polyvinyl chloride which, upon combustion release obnoxious and deleterious hydrochloric acid vapors or chlorine oxides. Additionally, incineration is subject to misoperation. In the typical incineration treatment, multiple chamber incineration is used utilizing a starved air main combustion chamber and afterburner to complete the combustion of the gases generated in the main chamber. Most such incineration systems utilize waste heat recovery and gas effluent treatments to avoid the discharge of any particulate matter. Unfortunately, however, the complexity of these incinerators renders them prone to maloperation, which can generate obnoxious odors and fumes. In severe circumstances, incomplete combustion resulting from faulty control of the afterburner section can form and spread airborne pathogens such as fungus spores and the like. For these reasons there is an increasing public sentiment against the siting and construction of new incinerators for this treatment. The industry thus needs a truly efficient and effective method for treatment of infectious waste that will provide assurances of sanitary treatment of such waste.

OBJECTIVES OF THE INVENTION

It is an objective of this invention to provide a method for the disposal of wastes.

It is a further object of this invention to provide a method for treatment of infectious waste that will render the waste sterile and in a condition for ultimate disposal.

It is an additional object of this invention to provide a method for the chemical and enzymatic treatment of infectious waste such as infectious hospital waste.

Other and related objectives will be apparent from the following description of the invention.

BRIEF STATEMENT OF THE INVENTION

The invention comprises the treatment of infectious hospital waste by a method which ensures virtually complete sterilization of the waste, generating a residue which is suitable for disposal by other methods. The infectious hospital wastes have a wide variety in composition and include bacteria, virus, yeast and molds, some of which such as yeast spores and viruses are extremely resistant to sterilization. Additionally, the wastes usually include troublesome solids such as blood vials and large limbs and tissue that must be comminuted to a satisfactory treatment size. The invention comprises a first step of digestion at elevated temperatures and under highly alkaline condition for one to three hours. This step is combined with the necessary comminution, e.g., grinding, pulverizing and the like, to ensure substantially complete liquefaction of the wastes. The liquid reaction products from the first step are neutralized to a slightly alkaline pH, e.g., 7.5–9.5, and the waste is then subjected to enzymatic digestion with a suitable proteolytic enzyme for a short period of time. Preferably this proteinase treatment is combined with further comminution to further reduce any oversized particles that may remain in the waste following the first treatment. The enzymatic treatment is continued for a period from 30 to 90 minutes at temperatures most suitable for the selected enzyme and results in substantially complete hydrolysis of the proteins in the waste. Finally, the treated waste from the second step of enzymatic digestion is inoculated with from 8 to 20 percent of a sterilant, preferably sodium hypochlorite and the pH is reduced to an acidic pH from about 3 to about 6, and the inoculated residue is held for an extended period of time, from about 30 to about 120 minutes at an elevated temperature to ensure essentially complete sterilization of the liquid. Thereafter the liquid is treated to render it suitable for efficient disposal, preferably by evaporative concentration using, as desired, multiple effect evaporators for thermal efficiency to generate a concentrated sludge which can, if desired, be dried to a powdered solid that can be disposed of in normal, non-hazardous waste landfills. If necessary, the solids can be held in quarantine until assayed for pathogens.

DESCRIPTION OF THE DRAWING

The invention will be described with reference to the FIGURE, which illustrates a suitable treatment apparatus for use in the method of this invention.

DESCRIPTION OF PREFERRED EMBODIMENTS

Infectious hospital wastes, commonly referred to as "red bag" waste, is a material of widely varying composition. Typically it includes plastics such as polyethylene, polyvinyl chloride, polystyrene, polymethyl methacrylate, etc., used for plastic tubes, containers, syringes, blood vials, and the like. Additionally, the waste contains blood, tissue and bone, occasionally of substantial size, exceeding one or two inches in maximum dimension. Other materials include cellulose products such as paper, cardboard and cloth, usually cotton.

The waste is contaminated with infectious pathogens including bacteria, virus, yeast and molds, some of which are extremely resistant to sterilization, such as Coccidiomycosis, which is resident in the soil in certain regions of the country and which is known to cause a life threatening disease commonly referred to as "Valley Fever".

The aforementioned "red bag" waste is treated in this invention to render it sterile and the treatment of the invention is redundant in sterilization treatments to ensure complete sterilization of the waste before it is released for ultimate disposal. The treatment of the invention comprises a three step process.

In the first step the waste is substantially completely liquified, sterilized and digested under bacteriologically severe conditions. In the second step, the waste is subjected to proteinaceous digestion with a suitable enzyme to break down the proteins of the waste into less refractory fragments. Thereafter, the waste is subjected to a second sterilizing treatment with a suitable sterilant, preferably a soluble hypochlorite salt, resulting in a sterile liquid containing approximately 20 weight percent solids. The treated and sterile liquid is then concentrated by evaporative concentration to obtain a sludge and/or solid powder which can be safely disposed in non-hazardous landfills or by other disposal treatments.

In the first step of the treatment the waste is comminuted by grinding and pulverizing to shatter containers such as blood vials and to reduce large bones and tissue fragments to a suitable size, i.e., having a maximum dimension of ½ inch or less. The comminuted waste is then subjected to a severe alkaline digestion. The digestion is performed by the addition of 5 to 10 volumes of 1 Normal caustic (sodium hydroxide) per volume of waste, resulting in a pH of the mixture having a value of from 11.0–13.5, and is a liquid mixture. The liquid mixture is heated to and maintained at a temperature of about 165° F. to 190° F., preferably 170° F. for a period from about 1–3, preferably 2, hours. This treatment results in substantially complete liquefaction of all tissue and bones in the waste and is sufficient to kill all of the pathogens contained in the waste. The treatment is conducted in the first stage shown in the flow diagram and the treatment can be practiced with a withdrawal of a slip stream of material under treatment continuously and passing that withdrawn material through a suitable comminution such as a hammer mill, disc grinder and the like. The comminuted stream from the grinder is continuously recycled to the alkaline digestion vessel.

As with all the treatments in the process, the digestion vessel is closed and has an entirely contained vapor recovery and condensation system to ensure that it does not create any airborne pathogens.

Following the alkaline digestion step, the liquid is withdrawn and passed to the protein digestion step. This step also can be combined with further size reduction treatment of any particulate matter which escapes in a granular form from the first treatment and, for this purpose, a second stage comminution step is practiced in a suitable grinder which also can be supplied with a slip stream withdrawn continuously from the second stage and recycled thereto during the treatment. The waste in the second stage is subjected to a protein digestion in the presence of a suitable proteinase, e.g., Alkylase 2.4 L. For this treatment, the stream from the first stage is partially neutralized by the addition of a strong acid, e.g., hydrochloric, sulfuric, nitric acid in a sufficient quantity to reduce the pH of the liquid to a value from about 7.5 to 9.5, preferably from 8 to 9 . The temperature of the liquid undergoing treatment in the second stage is maintained at the optimum pH for enzymatic activity, from about 120° to about 170°, preferably 150° F. The treatment is continued in the second stage for a period from about 30 to about 120, preferably 90, minutes, thereby ensuring complete digestion of the protein components of the waste mixture.

The aforementioned treatments in the first and second stages of the method of this invention are adequate to completely sterilize the mixture. To avoid, however, any possibility that the mixture may include some extremely refractory pathogen which, because of its durability or because of physical limitations in the grinding system, has escaped sterilization, a final sterilant treatment is included. The final stage is also practiced in a closed vessel, and the waste mixture is withdrawn from the second stage treatment vessel, acidified and passed to the sterilant treatment vessel. The waste is heated to and maintained to an elevated temperature from about 160° to about 180°, preferably 170°, F. in the sterilant vessel and 10 weight percent of a sterilant, preferably sodium hypochlorite, having a strength from about 10 to 25, preferably 16, weight percent is added to the waste mixture. The waste mixture is maintained at the aforementioned conditions from about 30 to about 90 minutes, preferably 60 minutes which is sufficiently severe to substantially destroy any residual pathogens that somehow have escaped sterilization in the preceding stages.

Following the last step of the sterilizing treatment of the invention, the treated waste is then further processed to facilitate its ultimate disposal. As the treated waste has a solids content of about 15 to about 30 weight percent, economical disposal dictates concentration of the waste to eliminate most of its water content. This is accomplished by evaporative concentration which can be processed in various conventional equipment including multiple-effect evaporators and atmospheric fluid bed driers and conical vacuum driers. For this purpose the treated waste is heated to a temperature of about 180° to 250° F. and passed into the evaporative concentrator or drier where substantially all of its water content can be eliminated. The treatment of this invention can be practiced in the equipment of the FIGURE in a batch processing.

Referring now to the FIGURE, there is illustrated a conventional dryer system which can be used to practice the invention. This dryer system is available from Processall, Inc. Cincinnati, Ohio, under the designation of DRYER U-MAX. It comprises a closed cylindrical vessel 10 lying on its side and equipped with a mixing paddles 12 attached to a shaft 14 driven by motor 16 and gear box 18. The waste is admixed with up to ten volumes of aqueous sodium hydroxide as described above for the first step and introduced through the charge port 19. The waste mixture is stirred and comminuted within the vessel, the comminution being accomplished by milling blades 20 which are within the vessel. Accurate weight of the material charged to the vessel is measured with load cells 22. Any vapors from the mixture are passed through a heated, pulse back filter 24 and passed to a condenser 26. The condensate is passed to a jacketed condensate drum 28 and the noncondensible vapor is passed to a vacuum pump 30, which maintains a reduced pressure on the system. The discharge 32 from the vacuum pump is passed to a secondary separator 34.

EXAMPLE 1

In this and subsequent examples, a hospital waste was synthesized by ingredients representative of the mix coming out of a red bag hospital mix. Although the composition of this waste varies tremendously within the same hospital and between hospitals, it is generally agreed that the amount of paper exceeds that of plastic, and that the paper and plastic, combined averages about 80 to 90 percent of the total waste. The plastic present in greatest amounts is polyvinyl chloride (PVC) and styrofoam is next greatest.

The synthetic mix in the experiments is 80 percent paper and plastic and 20 percent materials that are equivalent to body parts and body wastes. The three ingredients which are used to make up the body equivalent waste are:

a. Blood;
b. Four D Beef (chili grind)
    Mechanically deboned inedible beef, from animals which died in the field and delivered to a renderer; and
c. Dried Mulch.

The dried mulch is collected from planting beds, dried and standardized, and is added to the final mix to raise the bacteria count to 1,000,000 per gram.

The final mix which is used in the examples is:

| | |
|---|---|
| a. Mixture of different paper products | 50% |
| b. Mixture of different plastic products | 30% |
| c. Blood | 10% |
| d. 4D Beef | 9% |
| e. Standardized Mulch | 1% |
| TOTAL | 100% |

EXAMPLE 2

A determination of the severity of alkaline hydrolysis was made on waste animal tissue, while following the bacteria count through all steps of the experiment. In the experiments, the waste tissue is diluted 5 to 1 with water. The plastic and paper are omitted in the initial severity study to obtain more precise data on the level of bacteria in the solution being treated. The paper and plastic is omitted because the presence of these materials interferes with determination of bacteria counts in the solution. The following summarizes the waste tissue used in the experiments:

| | Three mixes under Test | | |
|---|---|---|---|
| Ingredients Etc | #1 | #2 | #3 |
| Water | 800 gms | 800 gms | 800 gms |
| 50% NaOH | 15 gms | 12 gms | 10 gms |
| Ground Beef | 100 gms | 100 gms | 100 gms |
| Blood | 100 gms | 100 gms | 100 gms |
| Inoculum #2 | 10 gms | 10 gms | 10 gms |
| Inoculum #3 | 10 gms | 10 gms | 10 gms |

The #2 inoculum contains 1 million heat resistant bacteria per gram and the #3 inoculum contains 100 million bacteria per gram. The inoculums are used at the 1 percent level, to insure a total bacteria count of over 1 million per gram after the addition of the water and a count of 10,000 per gram of heat resistant bacteria in the final mix.

The samples were prepared in a one liter laboratory container, heated to raise their temperatures to 160 degrees F., and covered with foil to minimize the loss of water vapor. The samples were then placed in a 160 degree forced air oven, and samples were pulled at the appropriate time and bacteria counts determined. The pH values of the samples were measured when prepared and after 2 hours of treatment. The values are listed below:

| | | | |
|---|---|---|---|
| Sample pH | 12.5 | 11.6 | 11.2 |
| pH after 2 hrs @ 160 F. | 12.2 | 11.2 | 11.0 |

I ran three levels an as is sample, a sample diluted 100 fold and a sample diluted 10,000 fold. The results appear in table #2

TABLE #2

| | Results of Bacteria Counts on the 12 Samples | | | |
|---|---|---|---|---|
| XXX | 15 minutes | 30 minutes | 60 minutes | 120 min |
| pH 11.0 | 8,000/ml | 5,000/ml | 3,000/ml | 4,000/ml |
| pH 11.6 | 15,000/ml | 7,000/ml | 3,000/ml | 4,000/ml |
| pH 12.2 | 500/ml | 300/ml | 100/ml | 15/ml |

The next series of tests will explore higher pH values with a control to see what effect heat alone has on the death rate of this mixture of bacteria.

EXAMPLE 3

In this series of experiments, the procedure of Example 2 will be repeated at higher pH values and with a control. The same waste formulas are used and the tests are sampled at the same time intervals. The temperature of the digestion was 160 degrees F. The following table summarizes the compositions of the samples:

TABLE #1

| | Ingredients in the four Samples Under Evaluation | | | |
|---|---|---|---|---|
| Ingredients | Control | #4 | #5 | #6 |
| Water | 800 gms | 800 gms | 800 gms | 800 gms |
| Blood | 100 gms | 100 gms | 100 gms | 100 gms |
| Ground Beef | 100 gms | 100 gms | 100 gms | 100 gms |
| Inoculum #2 | 10 gms | 10 gms | 10 gms | 10 gms |
| Inoculum #3 | 10 gms | 10 gms | 10 gms | 10 gms |
| 50% Caustic (NaOH) | none | 18 gms | 26 gms | 35 gms |

The pH values of the samples at the start of the digestion are as follows:

| | Control | #4 | #5 | #6 |
|---|---|---|---|---|
| Starting pH | 7 | 12.7 | 13.1 | 13.6 |

The results of the tests are summarized in the following table:

TABLE #2

| | Results of the Bacteria Counts on the Samples | | | |
|---|---|---|---|---|
| XXXXXXX | 15 minutes | 30 minutes | 60 minutes | 120 min |
| pH 7.0 | 100,000/ml | 80,000/ml | 70,000/ml | 15,000/ml |
| pH 12.6 | 200/ml | 30/ml | 0/ml | 0/ml |
| pH 13.1 | 0/ml | 0/ml | 0/ml | 0/ml |
| pH 13.6 | 0/ml | 0/ml | 0.ml | 0.ml |

The bacteria counts reported in the tests of Examples 2 and 3 are recalculated to indicate the percentage of bacteria killed for each bacteria count. The recalculated data are reported in the following table:

TABLE #1

| xxxxxxx | 15 | 30 | 60 | 120 |
|---|---|---|---|---|
| pH 7 | 90% | 92% | 93% | 98.5% |
| Ph 11 | 99.2% | 99.5% | 99.7% | 99.6% |
| Ph 11.6 | 98% | 99.3% | 99.7% | 99.6% |
| Ph 12.5 | 99.95 | 99.97 | 99.99 | 99.998 |
| Ph 12.6 | 99.98 | —.997 | —.998 | —.999 |
| Ph 13.1 | .999% | .999% | .999% | .999% |
| Ph 13.6 | .999% | .999% | .999% | .999% |

EXAMPLE 4

In the previous sets of experiments, several treatments were tried. The best seemed to be high levels of hypochlorite at neutrality. The high levels would bring a solution down from a million bacteria per gram to less than 500 per gram within two hours. One set of data indicated that an acid pH would increase the bacteria kill when coupled with hypochlorite. A second set of data indicated that propionic acid at a high level was also a good substitute for hypochlorite. In this series these two possibilities were checked out.

A series of experiments were conducted to treat a simulated red bag waste with sodium hypochlorite at three different levels, and with propionic acid at three different levels. In an additional experiment, both sodium hypochlorite and propionic acid were added to a caustic treated solution.

A total of 1.6 liters of a tissue premix, equivalent to red bag waste, was prepared, and its pH was adjusted to 4 by the addition of hydrochloric acid. The material was inoculated with 16 gms of both Inoculum #2 and #3, which insured a starting bacterial count of more than one million per gram.

The following table summaries the ingredients and conditions of the hypochlorite treatments:

TABLE

| INGREDIENTS | #1 | #2 | #3 | #4 | #5 | #6 | #7 | #8 |
|---|---|---|---|---|---|---|---|---|
| Red Bag Mix Ph 4 | 200 | 200 | 200 | 200 | 200 | 200 | 200 | 200 |
| 12% hypochlorite | 2 ml | 4 ml | 8 ml | 2 ml | — | — | — | — |
| Propionic Acid | — | — | — | 1 ml | 0.2 | 0.5 | 1.0 | — |
| Percent Hypochlorite | 1% | 2% | 4% | 1% | — | — | — | — |
| Percent Propionic | — | — | — | 0.5 | 0.1 | 0.25 | 0.5 | — |
| Temperature of Storage | 160 | 160 | 160 | 160 | 160 | 160 | 160 | 160 |

Samples were taken of each material under treatment at three time intervals. After 30 minutes of storage at 160 degrees F. in a forced air oven, a sample was removed and put up for bacteria counts. Two determinations were made; the first determination was on the undiluted sample, and the second determination was made after dilution 1 to 100 with distilled water.

At the end of two hours of the hypochlorite treatment, the sampling was repeated and again two determinations were made, as described above.

Thereafter, 200 milliliter samples of each material under treatment were brought up to a boil and a third bacteria count was determined, without any dilution of the sample. The bacteria counts determined are set out in the following tables:

TABLE

| | | Reagents and Bacterial Counts | | | | |
|---|---|---|---|---|---|---|
| No. | Treatment | 30 minutes as is 1–100 | | 2 Hrs as is 1–100 | | 2 Hrs + Boil as is |
| 1. | 1% Bleach | 160 | 16 | 19 | 1 | 20 |
| 2. | 2% Bleach | 23 | 0 | 2 | 0 | 0 |
| 3. | 4% Bleach | 30 | 0 | 0 | 0 | 0 |
| 4. | 1% Bleach & 0.5% Propionic | TNC | 200 | TNC | 10 | 30 |
| 5. | 0.1% Propioni | TNC | 50 | TNC | 40 | 120 |
| 6. | 0.25% Propionic | TNC | 60 | TNC | 20 | 80 |
| 7. | 0.5% Propionic | TNC | 60 | 170 | 30 | 30 |
| 8. | Control | TNC | 150 | TNC | 60 | 260 |

TABLE

| | | Time and Bacteria counts | | |
|---|---|---|---|---|
| SUN | TREATMENT | 30 Minutes | 2 hrs | 2 hrs + Boil |
| 1. | 1% Bleach | 1600/ml | 20/ml | 20/ml |
| 2. | 2% Bleach | 25/ml | 2/ml | 0 |
| 3. | 4% Bleach | 30/ml | 0 | 0 |
| 4. | 1% Bleach + 0.5% Propionic | 20,000/ml | 1,000/ml | 30/ml |
| 5. | 0.1% Propionic | 5,000/ml | 4,000/ml | 120/ml |
| 6. | 0.25% Propionic | 6,000/ml | 2,000/ml | 80/ml |
| 7. | 0.5% Propionic | 6,000/ml | 3,000/ml | 30/ml |
| 8. | Control, Negative | 15,000/ml | 6,000/ml | 250/ml |

TABLE
PERCENTAGE KILL OF THE DIFFERENT TREATMENTS

| SUN | TREATMENT | 30 MIN | 2 HRS | 2 HRS + BOIL |
|---|---|---|---|---|
| 1. | 1% BLEACH | 99.9% | 99.999% | 99.999% |
| 2. | 2% BLEACH | 99.999% | 99.9999% | 99.9999% |
| 3 | 4% BLEACH | 99.999% | 99.9999% | 99.9999% |
| 4 | 1% BLEACH + 0.5% PROPIONIC ACID | 98% | 99.9% | 99.99% |
| 5 | 0.1% PROPIONIC | 99.9% | 99.9% | 99.99% |
| 6. | 0.25% | 99.9% | 99.9% | 99.99% |
| 7. | 0.5% | 99.9% | 99.9% | 99.999% |
| 8. | CONTROL, NEGATIVE | 98.5% | 99% | 99.9% |

From the data, it is apparent that performing the hypochlorite treatment at a pH of 4 increases the kill dramatically over the treatment at a neutral or alkaline pH value, and the concentration of sodium hypochlorite necessary for a complete kill is reduced dramatically. Further, the use of both propionic acid and sodium hypochlorite does not increase the effectiveness of the treatment in killing bacteria. The use of propionic acid at levels below 0.5 weight percent does not kill the bacteria very effectively, and at least 0.5 percent propionic acid at boiling temperature is necessary for effective killing any residual bacteria after the caustic treatment.

EXAMPLE 5

Experiments were run to assess the effectiveness of the treatment to destroy resistant fungal agents including pathogens. A preparation consisting of a mixed culture of fungus such as the dermatophyte *T. rubrum*, a Candida which occurs in infections of the feet, a soil sample known to contain Coccidiomycosis, and several spore forming fungus including Aspergillus were placed in a one-liter Pyrex flask in the presence of paper, shredded latex gloves, other hospital plastics, and some toweling. All the experiments were carried out in a well ventilated hood. To the flask was added 5% sodium hydroxide until the materials were entirely covered with liquid, which required 250 milliliters solution.

The mixtures were heated to about 100 degrees C. for 15 minutes and then allowed to cool, and 6N sulfuric acid was added to bring the pH of the liquid to 9.0. The resultant mixture was a slush from the paper and cloth with discrete pieces of plastic and rubber.

Since there was no significant amount of proteinaceous matter present in the samples, the proteolytic digestion step of the treatment of this invention was omitted.

There was a total volume of about 400 ml. of sample, to which was added 10 grams calcium hypochlorite, and a reaction occurred for a few minutes and some additional liquefaction of the cellulose occurred. Sulfuric acid was added to reduce the pH of the liquid below 7. There was evidence of chlorine release, and the mixture was heated to 75 degrees C. for 10 minutes and then allowed to cool. Starch iodine paper showed that all the chlorine and hypochlorite had been discharged upon the further addition of a small amount of sodium bisulfite.

The mixture was boiled until most of the water was gone and the mixture was taken up to 1000 ml. with distilled water and checked again for hypochlorite and bisulfite. A portion was inoculated with *T. rubrum* and this portion and the main treated sample were cultured.

The *T. rubrum* inoculated sample showed growth in 5–6 days, the main sample showed no growth after incubation for five weeks. A separate test for coccidiomycosis showed no growth after four weeks.

Based on the experimental data, the process is capable of destroying the most resistant kind of organism that is known.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. The treatment of infectious hospital waste which comprises the steps of:
   a. providing infectious hospital waste which contains up to 35 weight percent plastics including chlorinated polymers, proteinaceous matter comprising bone, blood and tissue and spore-forming pathogenic microorganisms which comprises:
   b. mixing said infectious hospital waste with from 5 to 10 volumes of aqueous sodium hydroxide having a concentration from 0.5 to about 5.0 weight percent per volume of waste, sufficient to raise the pH of the mixture to a value of from 11.5–13, heating and maintaining the resultant liquid mixture at a temperature from about 165° F. to 190° F. for a period from about 1–3 hours to obtain a resultant liquid mixture; and
   c. neutralizing the resultant liquid mixture with a mineral acid to reduce the pH of the liquid mixture to a value from about 7.5 to 9.5, adjusting the temperature of the liquid mixture to 120° to 170° F., adding to the liquid mixture a proteinase enzyme, and maintaining the liquid mixture at the aforesaid temperature for a period from about 30 to about 120 minutes, sufficient to digest the proteinaceous matter in the waste and obtain a sterilized, protein-free, liquid residue substantially free of said pathogenic microorganisms.

2. The treatment of claim 1 including the additional step of subjecting the protein-free, liquid residue to further sterilization treatment by adding thereto from 5 to 15 weight percent of sodium hypochlorite, having a strength from about 10 to 25 weight percent, and heating the residue to and maintaining it a temperature from about 160° to about 180° F. for a period from about 30 to about 90 minutes, sufficient to completely sterilize the waste.

3. The method of claim 1 including the step of evaporative concentration of the residue to increase its solids content to a value from 10 to about 100 weight percent.

4. The method of claim 1 including the step of evaporating water from the residue to increase its solids content to greater than 50 weight percent.

5. The method of claim 4 including the step of evaporating water from the residue to form a dry solid.

6. The method of claim 5 including the step of discharging the dry solid to a non-toxic disposal site.

7. The treatment of claim 1 including the additional step of subjecting the sterilized, protein-free, liquid residue to further sterilization treatment by adding thereto at least 0.5 weight percent of propionic acid, and heating the residue to boiling.

8. The treatment of infectious hospital waste which comprises the steps of: providing infectious hospital waste which contains up to 35 weight percent plastics including chlorinated polymers, proteinaceous matter comprising bone, blood and tissue and spore-forming pathogenic microorganisms which comprises adding sufficient aqueous sodium hydroxide to the infectious hospital waste to prepare a pumpable mixture containing less than about 20% solids, said sodium hydroxide having a concentration sufficient to raise the pH of the pumpable mixture to above 11.5, heating and maintaining the resultant liquid mixture at a temperature from about 165° F. to 190° F. for a period from about 1–3 hours to obtain a resultant liquid mixture; and neutralizing the resultant liquid mixture with a mineral acid to reduce the pH of the liquid mixture to a value from about 7.5 to 9.5, adjusting the temperature of the liquid mixture to 120° to 170° F., and subjecting the liquid mixture to an enzymatic proteolytic digestion under conditions sufficient to digest the proteineous matter in the waste and obtain a sterilized, protein-free, liquid residue substantially free of said pathogenic microorganisms.

9. The treatment of claim 8 including the additional step of sterilizing the protein-free, liquid residue by the acidification of the residue to reduce its pH to at least 4.0 and the addition thereto of sodium hypochlorite having a strength sufficient to completely sterilize the residue.

10. The method of claim 9 including the step of evaporating water from the residue to increase its solids content to greater than 50 weight percent.

11. The method of claim 9 including the step of evaporating water from the waste to form a dry, solid residue.

12. The method of claim 11 including the step of discharging the dry solid residue to a non-toxic disposal site.

13. The treatment of claim 8 including the additional step of subjecting the sterilized, protein-free, liquid residue to further sterilization treatment by adding thereto at least 0.5 weight percent of propionic acid, and heating the residue to boiling.

* * * * *